(12) United States Patent
Chen (10) Patent No.: US 9,370,486 B2
(45) Date of Patent: Jun. 21, 2016

(54) NANOEMULSION COMPOSITION CONTAINING VITAMIN K

(71) Applicant: Latitude Pharmaceuticals Inc., San Diego, CA (US)

(72) Inventor: Andrew Xian Chen, San Diego, CA (US)

(73) Assignee: LATITUDE PHARMACEUTICALS INC., San Diego, CA (US)

( * ) Notice: Subject to any disclaimer, the term of this patent is extended or adjusted under 35 U.S.C. 154(b) by 0 days.

(21) Appl. No.: 13/688,161

(22) Filed: Nov. 28, 2012

(65) Prior Publication Data

US 2013/0189316 A1    Jul. 25, 2013

Related U.S. Application Data

(63) Continuation of application No. PCT/US2011/039188, filed on Jun. 3, 2011.

(60) Provisional application No. 61/350,986, filed on Jun. 3, 2010.

(51) Int. Cl.
| | |
|---|---|
| A61K 9/107 | (2006.01) |
| A61K 31/122 | (2006.01) |
| A61K 47/10 | (2006.01) |
| A61K 47/14 | (2006.01) |
| A61K 47/18 | (2006.01) |
| A61K 47/22 | (2006.01) |
| A61K 47/26 | (2006.01) |
| A61K 47/44 | (2006.01) |
| A61K 47/24 | (2006.01) |

(52) U.S. Cl.
CPC .............. *A61K 9/107* (2013.01); *A61K 9/1075* (2013.01); *A61K 31/122* (2013.01); *A61K 47/10* (2013.01); *A61K 47/14* (2013.01); *A61K 47/183* (2013.01); *A61K 47/22* (2013.01); *A61K 47/26* (2013.01); *A61K 47/44* (2013.01); *A61K 47/24* (2013.01)

(58) Field of Classification Search
CPC ....... A61K 47/14; A61K 47/10; A61K 47/22; A61K 31/122; A61K 31/5517
See application file for complete search history.

(56) References Cited

U.S. PATENT DOCUMENTS

| | | | |
|---|---|---|---|
| 4,840,970 A | 6/1989 | Ohasi et al. | |
| 5,023,271 A | 6/1991 | Vigne et al. | |
| 5,180,747 A | 1/1993 | Matsuda et al. | |
| 5,750,142 A * | 5/1998 | Friedman et al. | ............. 424/450 |
| 2002/0107265 A1 | 8/2002 | Chen et al. | |
| 2003/0170187 A1 | 9/2003 | Marchal | |
| 2004/0043043 A1 | 3/2004 | Schlyter et al. | |
| 2006/0067952 A1* | 3/2006 | Chen | ............................. 424/400 |
| 2007/0190064 A1 | 8/2007 | Speelmans et al. | |

FOREIGN PATENT DOCUMENTS

| | | |
|---|---|---|
| JP | 01-113315 A | 5/1989 |
| JP | 01113315 A | 5/1989 |
| JP | 01143830 | 6/1989 |
| WO | WO 2009-067734 A1 | 6/2009 |
| WO | WO2009067734 * | 6/2009 ............. A61K 47/44 |
| WO | WO 2011-153513 | 12/2011 |

OTHER PUBLICATIONS

The HLB system, a time saving guide to emulsifier selection, Chemmunique by ICI Americas Inc., 1980, Chapter 1, p. 2-3.*
Golding, J. et al., "Childhood cancer, intramuscular vitamin K, and pethidine given during labour," BMJ, Aug. 8, 1992;305(6849):341-6 (abstract).
Von Kries, R., "Neonatal vitamin K prophylaxis: the Gordian knot still awaits untying," BMJ, Jan. 17, 1998;316(7126):161-2 (abstract).
Wariyar, U. et al., "Six years' experience of prophylactic oral vitamin K," Arch Dis Child Fetal Neonatal Ed., Jan. 2000;82(1):F64-8 (abstract).

* cited by examiner

*Primary Examiner* — Bethany Barham
*Assistant Examiner* — Ping Cao
(74) *Attorney, Agent, or Firm* — Kilpatrick Townsend & Stockton LLP (57) ABSTRACT

In certain embodiments, this invention sets forth compositions, methods, and uses regarding a nanoemulsion composition that comprises a fat-soluble vitamin K and can therapeutically replace Phytonadione Injectable Emulsion, USP.

12 Claims, 5 Drawing Sheets

NANOEMULSION COMPOSITION CONTAINING VITAMIN K

CROSS-REFERENCES TO RELATED APPLICATIONS

This application is a continuation of PCT/US2011/039188, filed Jun. 3, 2011, which application claims priority to U.S. Provisional Patent Application No. 61/350,986, filed Jun. 3, 2010. The contents of the priority documents and all other references disclosed herein are incorporated in their entirety for all purposes.

BACKGROUND OF THE INVENTION

In certain embodiments, this invention sets forth compositions, methods, and uses regarding a nanoemulsion composition that comprise or consist essentially of a fat-soluble vitamin K and can therapeutically replace Phytonadione Injectable Emulsion, USP.

Vitamin K includes a group of lipophilic, hydrophobic vitamins that are required for blood coagulation. Chemically, they are 2-methyl-1,4-naphthoquinone derivatives. Vitamin $K_1$ is also known as phytonadione (also called phylloquinone or phytomenadione). Vitamin $K_1$ is found chiefly in leafy green vegetables and vitamin $K_2$ is found in meat, eggs, dairy, and natto, the Japanese fermented bean preparation. In adults, gut bacteria normally produce significant amounts of usable vitamin K. In newborns, the gut has not yet been colonized with bacteria. Therefore, standard medical practice in the US is to administer vitamin K injections prophylactically to prevent haemorrhagic disease of the newborn. Similarly, patients undergoing treatment with large doses of antibiotics may develop vitamin K deficiency due to a reduced intestinal flora. An injectable vitamin K preparation can be also used to prevent or treat this type of vitamin K defficiency.

The current vitamin K preparation for injection available in the U.S. is listed in the US Pharmacopeia as Phytonadione Injectable Emulsion, USP ("PIE-USP"). It is approved by the FDA for treating blood coagulation disorders including (1) prophylaxis and therapy of hemorrhagic disease of the newborn; (2) anticoagulant-induced prothrombin deficiency caused by coumarin or indanedione derivatives; (3) hypoprothrombinemia due to antibacterial therapy; (4) hypoprothrombinemia secondary to factors limiting absorption or synthesis of vitamin K; and (5) other drug-induced hypoprothrombinemia. An estimated 8 million doses of PIE-USP are administered in the US every year with about 50-60% of the doses used in newborns. The American Academy of Pediatrics Committee on Nutrition recommends that 0.5 to 1.0 mg Vitamin $K_1$ be administered to all newborns shortly after birth.

Since vitamin K is insoluble in water, a number of solubilization methods have been tried to dissolve it for injection. PIE-USP is an aqueous solution that contains polyoxyethylated fatty acid, which is a strong detergent (also known as Cremophor), to solubilize vitamin K. Originally developed by Merck & Co under the brand name of "AquaMEPHYTON®", Phytonadione Injectable Emulsion, USP actually does not contain any oil and is therefore not a true emulsion, despite what its name suggests. Other surfactants have also been used to solubilize vitamin K, including, for example, HCO-60 (Nikko Chemical Co., Ltd., Japan), which is also a high HLB (i.e., with a Hydrophobic-Lipophilic Balance value >7) surfactant or detergent that is similar to Cremophor.

The injection of a high HLB surfactant or detergent such as Cremophor, polysorbate 80 or HCO-60 can cause hypersensitivity reactions or, more severely, anaphylaxis. The potential for such sometimes fatal reactions is well documented for all Cremophor-containing drugs, such as TAXOL® and cyclosporine A. For this reason, the package insert for PIE-USP bears an FDA black box warning noting that the drug may be very unsafe or even fatal if injected intravenously or intramuscularly (AquaMEPHYTON® package insert. Merck & Co., February 2002). Moreover, Cremophor has been linked to childhood cancer (Golding, J. 1992. BMJ 305: 341) and acute lymphoblastic leukemia (von Kries, R. 1998. BMJ 316: 161; Wariyar, U. et al. 2000. Arch Dis Child Fetal Neonatal Ed 82: F64). Needless to say, such associations would be terrifying to both parents and physicians. Furthermore, Cremophor-containing PIE-USP has potential to cause pain and irritation at the injection site when injected subcutaneously or intramuscularly and may cause gastrointestinal disturbance if taken orally. Such irritation is believed related to the hemolytic nature of Cremophor.

A safer replacement for PIE-USP is needed. Nevertheless, even after many years of PIE-USP usage, a new and safer composition has still not been developed in the US. The investment and return economics related to the small market size and high cost of obtaining marketing approval for such a new composition are key reasons why a new and safer composition has not yet been developed for the US market. The current market size for PIE-USP is about $25 million per year, which is too small for most drug developers to justify the cost of obtaining a new drug approval in the US (estimated to be several hundred million dollars). This unfavorable return on investment ratio discourages drug developers from bringing a safer vitamin K injectable product to the market while patients, including nearly every newborn in the US, continue to be exposed to potentially severe adverse effects of Cremophor.

This application discloses embodiments of a new nanoemulsion composition that could make a safer replacement for PIE-USP commercially feasible by significantly reducing its development cost. By having bioequivalent properties, the new composition may be approved by the FDA on the basis of a single human pharmacokinetic study demonstrating their bioequivalence. Such abbreviated approval requirements based on pharmacokinetic and bioequivalent properties is codified in US Federal Law as a 505(b)(2) New Drug Application (NDA). An abbreviated and accelerated market approval may require only about 30 patients, which translates into a significant reduction in development cost making the development of a safer replacement for PIE-USP a commercially viable possibility.

Preferably, the nanoemulsion composition disclosed herein has a surprising pharmacokinetic profile that is nearly identical to the PIE-USP (i.e., "bioequivalent"). This new composition achieves this property without the use of Cremophor or any other high HLB surfactant for solubilizing vitamin K.

More preferably, the nanoemulsion composition disclosed herein does not cause hypersensitivity or anaphylactic reactions, is not hemolytic (and therefore has a low potential for causing pain and irritation at the injection site), and has stability comparable to PIE-USP (Example 12). These safety and stability features, when combined with their bioequivalent properties, form the basis for a commercially feasible safe replacement for PIE-USP and sets these nanoemulsion embodiments apart from any other compositions in the prior art.

Ohasi, et al. (U.S. Pat. No. 4,840,970) discloses an aqueous solution composition for vitamins A, E and K comprising hydrogenated lecithin in the amount of 0.1 to 12 parts by weight of the vitamin. The composition disclosed by Ohasi is an "aqueous solution" that contains no oil and is therefore not an oil-in-water emulsion or nanoemulsion by strict definition. The disclosed hydrogenated lecithin-to-vitamin K weight ratio of 0.1:1 to 12:1 is considerably lower than the 13:1 to 25:1 of phospholipid-to-vitamin K weight ratio used for the nanoemulsion embodiment. Moreover, Ohasi did not teach any method or composition for achieving bioequivalence to PIE-USP.

Ida et al. (U.S. Pat. No. 5,021,570) disclosed another aqueous solution comprising hydrogenated lecithin, a triester of glycerol with fatty acids having 8 to 12 carbons, the monoester of the same, a triester of glycerol with oleic acid, stearic acid or palmitic acid, and water. The composition so disclosed was an "aqueous solution" and was not an emulsion or nanoemulsion. The disclosed concentration for hydrogenated lecithin was about 0.05 to 3%, which is considerably lower than the 4-20% concentration of phospholipid used for the nanoemulsion embodiments of the present invention. Furthermore, the exemplary nanoemulsion embodiments do not contain any monoester of glycerol. Moreover, Ida did not teach any method or composition for achieving bioequivalence to PIE-USP.

Vitamin K is photosensitive and can decompose in the presence of light. Matsuda, et al. (U.S. Pat. No. 5,180,747) teaches a method of protecting vitamin K in the presence of light and preventing the reduction in activity of a fat-soluble vitamin K composition that comprises α-carotene, γ-carotene, lycopene, and canthaxanthin. However, the exemplary nanoemulsion embodiments do not contain any of these ingredients.

Kaneshiro (JP 11438300) discloses oil-in-water emulsion compositions for vitamin K1 and K2 comprising egg lecithin and oil, wherein a weight ratio of the phospholipid to vitamin K is about 0.5:1 to 10:1 and preferably 1:1 to 5:1. Preferred embodiments of the present invention's nanoemulsion composition comprise vitamin K, a phospholipid component and an oil component, but with a weight ratio of phospholipid to vitamin K of about 13:1 to 25:1.

BRIEF SUMMARY OF THE INVENTION

In certain embodiments, the present invention sets forth a safe and commercially feasible injectable composition for vitamin K that is (a) bioequivalent to the marketed product it is intended to replace (i.e., PIE-USP), (b) free of any allergenic or irritating agents, specifically Cremophor or surfactants of high HLB value, (c) sufficiently stable to provide an acceptable shelf life, (d) composed of small oil droplets and filterable though a 0.2-micron filter, and (e) transparent or translucent.

Preferably, the present invention sets forth a nanoemulsion composition that fulfills all of the aforementioned properties, wherein said nanoemulsion comprises vitamin K at from about 0.1 to 2% (more preferably, 0.2 to 1%), a phospholipid-to-vitamin K weight ratio of about 13:1 to 25:1, and an oil content of about no more than 1% by weight of the composition.

The nanoemulsion composition disclosed herein is an oil-in-water emulsion comprising, consisting essentially of, or consisting of vitamin K at about 0.2 to 1%, soybean oil at about 0.5% to 2%, a medium-chain triglyceride at about 0.5 to 2%, a phospholipid at about 4 to 25% and sucrose at about 10% (all percentages based on the total weight of the composition), wherein the phospholipid-to-vitamin K weight ratio is about 13:1 to 25:1.

The present nanoemulsion composition is significantly different from PIE-USP or other vitamin K injectable compositions disclosed in the prior art. PIE-USP contains Cremophor as a solubilizer and is free of soybean oil, medium-chain triglycerides or phospholipids.

It is worth noting that the concentration of phospholipid (4-20%) or the weight ratio of phospholipid-to-vitamin K (13:1 to 25:1) in the present nanoemulsion is extraordinarily high and is significantly above the ranges disclosed in the prior art. The nanoemulsion composition of the present invention is therefore novel in light of the prior art.

The high phospholipid concentration or phospholipid-to-vitamin K ratio of the present nanoemulsion produced a pharmacokinetic (PK) profile that was unexpectedly bioequivalent to PIE-USP. Establishing that a new vitamin K formulation has a bioequivalent PK profile is very advantageous for developing a replacement product for PIE-USP.

In fact, it is very unusual for an emulsion to be bioequivalent to a surfactant-containing composition such as PIE-USP. There is no prior art that teaches any emulsion composition or method of accomplishing such goal for a vitamin K or other drug. In certain embodiments, the nanoemulsion of this invention achieves the unexpected bioequivalence to PIE-USP by comprising (1) A high phospholipid-to-drug ratio (i.e. 13:1 to 25:1), and (2) A very low oil content (i.e., no more than about 1%).

A nanoemulsion comprising these two unique compositional features tends to have much smaller droplet size (e.g., about 100 nm, as shown in Example 6) as compared to a typical emulsion for intravenous injection, which does not have a high phospholipid-to-drug ratio and a low oil content. A good example of a typical emulsion for intravenous injection is the DIPRIVAN® (propofol) Injectable Emulsion, which contains a phospholipid-to-drug ratio of 1.2:1 (12 mg/mL phospholipid and 10 mg/mL drug) and a high oil content (10%) with an average droplet size of about 300-400 nm or larger.

Without intending to be bound by theory, the exceptionally small droplets may endow the nanoemulsion with solution-like behavior in terms of its circulation in the blood stream and organ distribution. With the typical capillary vessel of about 5-10 microns in diameter and the nanoemulsion droplets being less than 200 nm, this should enable the nanoemulsion droplets to circulate freely in even the smallest blood vessels to the same extent as a solution. At the same time, the low oil content of the nanoemulsion may also eliminate the possibility of altering the plasma profile or tissue disposition of vitamin K. Oils are naturally metabolized by lipases, which are ubiquitous in the body, and the small amount of oil in the nanoemulsion of the current invention may be rapidly broken down in just a few minutes, which would rapidly release vitamin K from the droplets. And, once released, the vitamin K molecules would behave similarly to a solution formulation such as PIE-USP. The combination of (1) a high phospholipid-to-vitamin K ratio with (2) very low oil content is not found in the prior art.

The small droplets produced by the nanoemulsion comprising (1) a phospholipid-to-drug ratio in between about 13:1 to 25:1 and (2) a low oil content of no more than about 1% also permit the composition to pass through a 0.2-micron filter, thus allowing sterilization by filtration. This is not possible for the aqueous solution or other prior art emulsion compositions disclosed by Ohasi (U.S. Pat. No. 4,840,970), Ida (U.S. Pat. No. 5,021,570) or Kaneshiro (JP 11438300), which are not filterable through 0.2 micron filters due to their large droplet size. Such large-particle emulsions therefore can only rely on high temperature autoclaving for sterilization. Vitamin K is also prone to oxidation. Therefore, autoclaving is impractical for vitamin K compositions and will be very likely to degrade any vitamin K composition.

In addition, the nanoemulsion of the present invention is translucent with a light transmittance of greater than 20% (measured at 600 nm (T600) or 750 nm (T750)). In contrast, it is well known in the art of pharmaceutical drug formulations that most emulsions are dense, opaque white compositions (with the light transmittance less than 5-10%), which can obscure the visual detection of bacterial and fungal contaminants as well as contaminants from other foreign particles (Madsen, R. et al. 2009, Pharmacopeial Forum, Vol. 35: 1383). Such contaminants are potentially dangerous, especially when the drug formulation is administered intravenously to a patient. Injected particulate matter can obstruct blood vessels and lead to pulmonary emboli or thrombosis. The transparency or near transparency of the nanoemulsion of the present invention (FIG. 1) will permit visual examination, which will greatly reduce the safety risks associated with particular matter.

Moreover, the very low oil content in the nanoemulsion of the present invention reduces the potential for hyperlipidemia, a serious medical condition of elevated blood triglyceride levels that can lead to atherosclerosis, coronary heart disease, and stroke.

The high phospholipid-to-vitamin K ratio and very low oil content used in the nanoemulsion of the present invention enabled the formation of extremely small droplets form the basis of a uniquely transparent composition with advantageous solution-like PK and filterability properties that are not found in, taught by or can be anticipated by any prior art.

These and other aspects, embodiments and objects will be more apparent when read with the detailed description and figures which follow.

BRIEF DESCRIPTION OF THE DRAWINGS

Bottom panel: From left to right are Tubes #1, 2, 3, 4, 5, 6, 7, 8, 9 and 10. Tubes 1-8 contain PIE-USP at the same corresponding concentrations as in the F2 nanoemulsion-containing tubes, Tube #9 is normal saline (negative control) and Tube #10 is water (positive control). The PIE-USP caused hemolysis in Tubes #4, 5, 6, 7 and 8, corresponding to vitamin K1 concentration of 0.16, 0.2, 0.4, 0.6 and 1 mg/mL, respectively.

DETAILED DESCRIPTION OF THE INVENTION

The nanoemulsion of the present invention is a slightly yellow, transparent or translucent composition, which comprises oil droplets of an average size of less than 200 nanometers in diameter, or more preferably, less than 100 nm. The nanoemulsion is stable and has an excellent long-term stability (Example 6). Chemically it maintains the integrity of vitamin K1 and physically, it remains transparent or translucent, maintaining the same nanometer droplet size upon prolonged storage (e.g., 24 months). More particularly, the nanoemulsion is characterized by high light transmittance at 600/750 nm and small droplet size, even after storage at 25° C. for 6 months or after a freeze-thaw treatment. Such stability properties, which are very advantageous for a commercially feasible drug product, are not found in any aqueous solution or emulsion compositions disclosed in the prior art. Biologically, the nanoemulsion is non-allergenic, does not cause hypersensitivity or anaphylactic reactions, is non-hemolytic and is bioequivalent to PIE-USP.

The term "nanoemulsion" used herein includes an oil-in-water emulsion having oil droplets that are exceedingly small in size, i.e., less than 200 nm or preferably 100 nm, and having a high transparency with light transmittance at 600 nm or 750 nm of no less than 20% or preferably 50%. In certain embodiments, the oil droplet size is about 75 nm-200 nm, such as 75 nm to 150 nm, or 75 nm to 115 nm. In certain embodiments, the oil droplet size is about 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, 150 nm, 155 nm, 160 nm, 165 nm, 170 nm, 175 nm, 180 nm, 185 nm, 190 nm, 195 nm, or 200 nm.

In certain embodiments, a nanoemulsion of this invention solubilizes the lipophilic vitamin K presumably in those droplets. Physically, a nanoemulsion has significant differences compared to regular oil-in-water emulsions. For example, a nanoemulsion is transparent (i.e., with a high T600/T750 light transmittance value) and has a solution-like appearance whereas a regular emulsion is milky-white and opaque with T600/T750<20%. The average droplet size of a nanoemulsion is much below the average droplet size of a regular oil-in-water emulsion, for which the average droplet diameter is usually greater than 300-400 nm. And finally, the nanoemulsion exhibits far better stability than a regular oil-in-water emulsion with minimal changes in the transparency or droplet size after being stored at 25° C. or 2-8° C. for 6 months or after a freeze-thaw treatment. Most surprisingly, in certain preferred embodiments the nanoemulsion of this invention is bioequivalent to the commercial product PIE-USP—a property that no other emulsion has yet matched.

"Phytonadione Injectable Emulsion, USP" refers to a sterile, aqueous dispersion of phytonadione. Prior to Feb. 1, 2005, it was labeled as "Phytonadione Injection, USP". Merck & Co. initially developed PIE-USP under the brand name of "AquaMEPHYTON®" which contains 10 mg/mL phytonadione, 70 mg/mL polyoxyethylated fatty acid derivative (Cremophor), 37.5 mg/mL, 9 mg/mL benzyl alcohol and water. It is worth noting that Phytonadione Injectable Emulsion, USP does not contain any oil in its composition and is technically not an oil-in-water emulsion despite what its name suggests. Rather, using a strict physical chemistry definition, PIE-USP should be defined as an aqueous solution, since all components are dissolved in water.

As an aqueous solution, PIE-USP is sensitive to freezing stress. Upon freezing and thawing, AquaMEPHYTON® or its generic equivalent will form two phases with the Cremophor separating out. A phase separated preparation is unsafe for intravenous injection as its larger droplets could form blockages in capillaries, resulting in an embolism. Therefore, storage conditions for PIE-USP must be carefully controlled to prevent accidental freezing. In contrast, in certain preferred embodiments the nanoemulsion of this invention is robust and retains its properties after a freeze-and-thaw cycle. That is, the average droplet size or the light transmittance of the nanoemulsion of the current invention remained essentially unchanged after a freeze-and-thaw stress. In certain preferred embodiments, the nanoemulsion of this invention, being an oil-in-water emulsion, is therefore different from PIE-USP in its composition, physical form and stability after a freeze-and-thaw cycle (Example 12).

The term "vitamin K" as used herein includes a group of lipophilic, hydrophobic vitamins that are needed for the post-translational modification of certain proteins, mostly required for blood coagulation. Chemically, they are 2-methyl-1,4-naphthoquinone derivatives. Vitamin $K_1$ is also known as phylloquinone or phytomenadione (also called phytonadione), and vitamin $K_2$ is also known as menaquinone or menatetrenone. There are three synthetic forms of vitamin K, vitamins $K_3$, $K_4$, and $K_5$, which are used in many areas including the pet food industry (vitamin $K_3$) and for inhibiting fungal growth (vitamin $K_5$).

The term "light transmittance (%)" as used herein is a measurement of transparency of the nanoemulsion and is defined as the fraction of incident light at a specified wavelength (i.e., 600 nm) that passes through a sample. It is calculated using the following equation:

$$T_\lambda = I \div I_0 \times 100$$

where $I_0$ is the intensity of the incident light and I is the intensity of the light coming out of the sample and $T_\lambda$ is transmittance. The $T_\lambda$ value can be readily measured by a UV-visible spectrophotometer at a fixed wavelength. A visible wavelength such as 600 or 750 nm is commonly used to obtain the T600 or T750 values.

Figure 1:
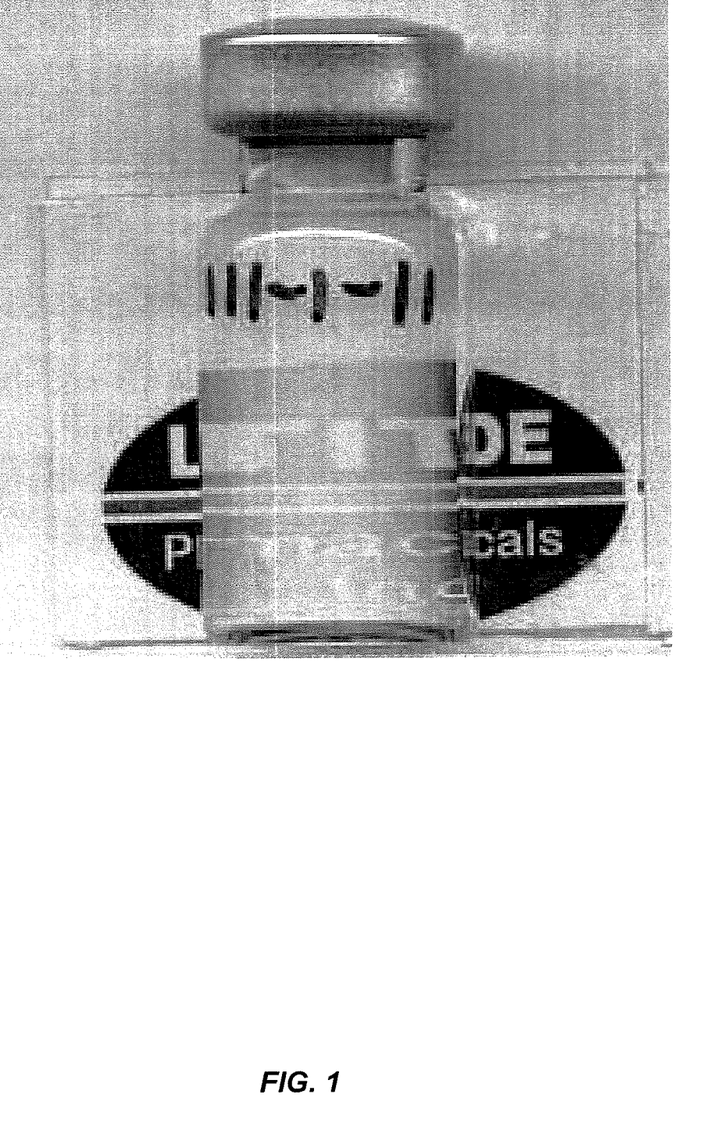
FIG. 1. The translucent appearance of the nanoemulsion prepared according to Example 1 is shown.
Figure 2:
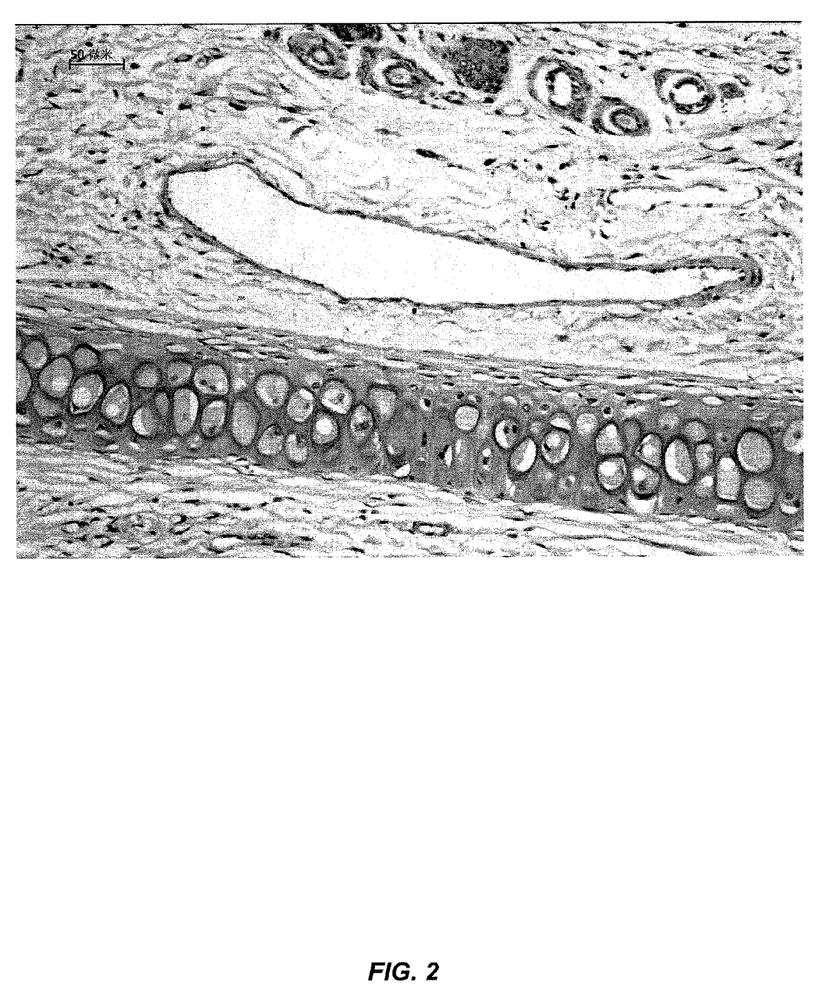
FIG. 2. Histopathologic image of a rabbit marginal ear vein after infusion with a vitamin K1 nanoemulsion (F1 according to Example 1). A thin vein wall is readily visible with an inner endothelium cell lining. The vessel lumen contains red blood cells. No edema is observed for the vein wall and no inflammatory cell infiltration has occurred into the surrounding area.

The light transmittance value of an emulsion is directly related to its droplet size and can be used to differentiate certain preferred embodiments of the nanoemulsion of this invention from a regular emulsion. For a conventional emulsion such as milk or a fat emulsion for intravenous injection such as INTRALIPIDT™, the light transmittance value measured at 600 nm/750 nm wavelength is generally less than 5-10% (such as up to 0.5, 1, 2, 3, or 4%; or alternatively, up to 5, 6, 7, 8, 9, or 10%), which is due to the light-reflecting white and opaque properties of these emulsions. The nanoemulsion of the current invention is, however, characterized by a very high transmittance of greater than 20% and is nearly transparent (FIG. 1).

The term "Cremophor" as used herein is the registered trademark of BASF Corp. for its version of polyethoxylated castor oil. It is prepared by reacting 35 moles of ethylene oxide with each mole of castor oil. The resulting product is a mixture of castor oil molecules with differing degrees of polyethoxylation (CAS number 61791-12-6). Cremophor is a synthetic, nonionic surfactant and its pharmaceutical utility comes from its ability to stabilize emulsions of nonpolar materials in aqueous systems. Cremophor is an excipient or additive in drugs. Cremophor and some other surfactants of high HLB values (meaning soluble in water) such as polysorbate 80 are known to cause hypersensivity or anaphylaxis when injected intravenously. Such allergic reactions are well documented for a number intravenously-administered drugs that contain Cremophor or polysorbate 80, such as TAXOL for the latter.

The term "bioequivalent" as used herein includes a plasma concentration-over-time pharmacokinetic (PK) profile that coincides with the PK profile of a reference drug. As used herein, the term includes the coinciding and nearly identical PK profile from a vitamin $K_1$ nanoemulsion composition of certain preferred embodiments of this invention and the corresponding PK profile for PIE-USP following an intravenous, intramuscular or subcutaneous injection in a selected animal or human model (e.g., see FIGS. 4 and 5).

The nanoemulsion composition of this invention comprises a vitamin K at from about 0.1 to 2% (such as about 0.18, 0.2, 0.22, 0.5, 0.8, 1.0, 1.2, 1.5, 1.8, or 2%), preferably from about 0.2 to 1% (such as about 0.18, 0.2, 0.22, 0.3, 0.4, 0.5, 0.6, 0.7, 0.8, 0.9, 1.0 or 1.1%), a phospholipid at a phospholipid-to-vitamin K weight ratio of about 13:1 to 25:1 (such as 13:1, 14:1, 15:1, 16:1, 17:1, 18:1, 19:1, 20:1, 21:1, 22:1, 23:1, 24:1, or 25;1), and an oil at no more than 1% by weight of the emulsion weight (such as up to about 1, 0.9, 0.8, 0.7, 0.6, 0.5, 0.4, 0.3, 0.2, or 0.1%).

The terms "a," "an," or "the" as used herein not only includes aspects with one member, but also aspects with more than one member. For example, an embodiment including "a phospholipid and a triglyceride oil" should be understood to present aspects with at least a second phospholipid, at least a second triglyceride oil, or both.

The term "about" as used herein to modify a numerical value indicates a defined range around that value. If "X" were the value, "about X" would generally indicate a value from 0.8X to 1.2X, and more preferably, 0.9X to 1.1X. Any reference to "about X" specifically indicates at least the values X, 0.90X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.10X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1. When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9, or 11%" is equivalent to "about 7%, about 9%, or about 11%."

In general, embodiments described herein that include chiral compounds may include embodiments with the racemic form or embodiments enriched in the D- or L-enantiomer thereof.

The term "or" as used herein should in general be construed non-exclusively. For example, an embodiment of "a composition comprising A or B" would typically present an aspect with a formulation comprising both A and B. "Or" should, however, be construed to exclude those aspects presented that cannot be combined without contradiction (e.g., a formulation pH that is between 9 and 10 or between 7 and 8).

Generally, when a percentage range is taught, it incorporates all full or partial percentages in between (i.e., within the bounds of the range). For example, a percentage range of 5 to 20% would also teach inter alia the specific values of 7.15% and 17%. A percentage range of about 0.5 to 2% would also teach inter alia the specific values of 1.37%, 1.2%, and 0.63%.

The term "soybean oil" as used herein includes refined oil extracted from soybean. For injection use, such oil must pass certain quality specifications including purity, microbiological and endotoxin limits, meeting certain compendial standards and be manufactured in a facility meeting cGMP standards. In certain embodiments, the concentration of the oil is no more than 1%, such as about 0, 0.1, 0.2, 0.3, 0.4, 0.5, 0.6, 0.7, 0.8, 0.9, or 1.0%.

In certain embodiments, other vegetable oils including, but not limited to, almond oil, borage oil, black currant seed oil, corn oil, safflower oil, soybean oil, sesame oil, cottonseed oil, peanut oil, olive oil, rapeseed oil, coconut oil, palm oil, canola oil, etc. may be used as well. The specific type of vegetable oil used (e.g., soy bean oil, corn oil, or safflower oil, etc.) is not critical, so long as it is safe, well tolerated, pharmaceutically acceptable, chemically stable and can be formed into droplets having a desired size range.

The term "medium chain triglyceride" (MCT) as used herein includes another class of triglyceride oil that can be either naturally derived or synthetically produced. MCTs are made from fatty acids that are usually about 8 to about 12 carbons in length. Like vegetable oils, MCTs have been used extensively in injectable emulsion preparations as a source of calories for patients requiring parenteral nutrition. Such oil is commercially available as Miglyol 812 from SASOL GmbH, Germany, CRODAMOL GTCC-PN from Croda, Inc. of Parsippany, N.J., or Neobees M-5 oil from PVO International, Inc., of Boonton, N.J. Other low-melting medium chain oils may also be used in the present invention. In certain embodiments, the concentration of MCT is no more than 1%, such as about 0, 0.1, 0.2, 0.3, 0.4, 0.5, 0.6, 0.7, 0.8, 0.9, 1.0%).

In certain embodiments, the vegetable oil to MCT oil ratio is within a range of about 2:1 to about 1:2 (such as about 2:1, 1.9:1, 1.8:1, 1.7:1, 1.6:1, 1.5:1, 1.4:1, 1.3:1, 1.2:1, 1.1:1, and 1:1) and preferably about 1:1.

The term "phospholipid" as used herein includes a triester of glycerol with two fatty acids and one phosphate ion. Exemplary phospholipids useful in the present invention include, but are not limited to, phosphatidyl chlorine, lecithin (a mixture of choline ester of phosphorylated diacylglyceride), phosphatidylethanolamine, phosphatidylglycerol, phosphatidic acid with about 4 to about 22 carbon atoms, and more generally from about 10 to about 18 carbon atoms and varying degrees of saturation. The term "phospholipid" used herein can be either a single phospholipid or a mixture of several phospholipids.

The phospholipids useful in the present invention can preferably be of natural origin for enhanced safety. Naturally occurring phospholipids include soy lecithin, egg lecithin, hydrogenated soy lecithin, hydrogenated egg lecithin, sphingosine, gangliosides, and phytosphingosine and combinations thereof. Phospholipids can also be synthesized and the common synthetic phospholipids may include but are not limited to diacylglycerols, phosphatidic acids, phosphocholines, phosphoethanolamines, phosphoglycerols, phosphoserines, lysophospholipids, and pegylated phospholipids. In certain embodiments, the concentration of phospholipid is 4 to 25%, such as about 4, 5, 6, 7, 8, 9, 10, 11, 12, 13, 14, 15, 16, 17, 18, 19, 20, 21, 22, 23, 24, or 25%).

In certain embodiments, the nanoemulsion of the present invention may further contain pharmaceutically acceptable additives including, but not limited to, acidifying, alkalizing, buffering, chelating, complexing and solubilizing agents, antioxidants and antimicrobial preservatives, suspending and/or viscosity modifying agents, tonicity modifying agents, cryo-protectants, and other biocompatible materials or therapeutic agents. In certain embodiments, such additives assist in stabilizing the nanoemulsion and rendering sufficient shelf life to the compositions of the present invention.

In certain embodiments, the nanoemulsion of the present invention has an osmolality of approximately 300 to 500 mOsm and may include potassium or sodium chloride, trehalose, sucrose, sorbitol, glycerol, mannitol, polyethylene glycol, propylene glycol, albumin, amino acid and mixtures thereof.

The term "antioxidants" as used herein preferably includes metal ion chelators and/or reducing agents that are safe to use in an injectable product. A metal ion chelator works as an antioxidant by binding to metal ions and thereby reduces the catalytic effect of metal ions on the oxidation reaction of the test substance. Metal chelators that are useful in certain embodiments of this invention may include EDTA, glycine and citric acid or salts thereof.

Reducing agents achieve their antioxidant effect by reacting with oxidizing agents in competition with test substance or by converting the oxidized test substance back to the original test substance in the reduced form. The reducing agents useful in certain embodiments of this invention include, but are not limited to, methionine, cysteine, glutathione, ascorbic acid or salts thereof, ascorbyl palmitate, sodium metabisulfite, propyl gallate, butylated hydroxyanisole, butylated hydroxytoluene, tocopherol, histidine, amino acids or salts thereof, reducing sugars or any mixtures thereof.

The term "cryo-protectant" as used herein includes any of the safe and biocompatible agent(s) that protect the nanoemulsion during freezing by keeping the sub-micron size droplets separate in the surrounding milieu. The cryo-protectants useful for certain embodiments of the present invention include, but are not limited to, monosaccharides, disaccharides, polysaccharides, propylene glycol, polyethylene glycol, glycerol, poly-ols, dextrins, cyclodextrins, starches, cellulose and cellulose derivatives, proteins, peptides, amino acids, sodium chloride, polyvinypyrrolidone, or mixtures thereof. For instance, in certain embodiments, the cryo-protectant is mannitol, sorbitol, xylitol, lactose, fructose, xylose, sucrose, trehalose, mannose, maltose, dextrose, dexstrane, or a mixture thereof. In certain embodiments, the cryo-protectant is sucrose, a combination of sucrose and mannitol, or a combination of sucrose and trehalose. In certain embodiments, the formulations of the present invention do not comprise gum acacia.

The term "injectable" as used herein includes the acceptance of an ingredient by a drug regulating authority (e.g., the US FDA) permitting its use in an injection drug.

In certain embodiments, the present compositions are both chemically and physically stable. A composition is "chemically stable" if the drug, e.g., vitamin K, in the composition is not substantially chemically degraded after storage under appropriate conditions for at least one month. In certain embodiments, the concentration of the intact vitamin K in the composition is reduced by less than about 5% under appropriate storage conditions (e.g., at −20° C., 2-8° C., or at room temperature) for at least 6 months.

As used herein, a nanoemulsion composition is "physically stable" if it can be stored under appropriate conditions for at least 6 months without an increase in its average particle size by more than 100%, or without evidence of phase separation, creaming, or particle aggregation. In certain embodiments, the average size of particles of a composition of the present invention does not increase by more than about 10%, 20%, 25%, 30%, 40%, 50%, 75%, or 100% under appropriate storage conditions (e.g., at −20° C., 2-8° C., or room temperature) for at least 6 months.

Therapeutic Uses

The compositions described herein are especially useful for treating blood coagulation disorders including (1) prophylaxis and therapy of hemorrhagic disease of the newborn; (2) anticoagulant-induced prothrombin deficiency caused by coumarin or indanedione derivatives; (3) hypoprothrombinemia due to antibacterial therapy; (4) hypoprothrombinemia secondary to factors limiting absorption or synthesis of vitamin K; and (5) other drug-induced hypoprothrombinemia.

Acquired coagulation disorders are the result of conditions or diseases, such as vitamin K deficiency, liver disease, disseminated intravascular coagulation (DIC), or development of circulation anticoagulants. The defects in blood coagulation are the result of secondary deficiencies in clotting factors caused by the condition or disease. For example, production of coagulation factors from the liver is often impaired when the liver is in a diseased state. Along with decreased synthesis of coagulation factors, fibrinolysis becomes increased and thrombocytopenia (deficiency in platelets) is increased. Decreased production of coagulation factors by the liver also can result from fulminant hepatitis or acute fatty liver of pregnancy. Such conditions promote intravascular clotting which consumes available coagulation factors. The compositions provided herein can be used in the treatment of acquired coagulation disorders in order to alleviate deficiencies in blood clotting factors.

Patients undergoing anticoagulant therapies for the treatment of conditions, such as thromboembolism, can exhibit bleeding episodes upon acute administration of anticoagulants or develop hemorrhagic disorders as a result long term usage of such therapies. The compositions provided herein are useful for treatments for such bleeding episodes which typically include administration of procoagulants. The compositions provided herein can be used in treatments to control bleeding episodes in patients with acquired bleeding disorders due to anticoagulant treatments.

The invention will now be described in greater detail by reference to the following non-limiting examples.

Example 1

Preparation of F1 Nanoemulsion Containing Vitamin K1

A nanoemulsion containing 0.2% vitamin K1 was prepared using the following composition and procedure:

| F-1 composition | |
|---|---|
| Ingredient | % w/w |
| Phytonadione | 0.2 |
| Soybean oil | 0.5 |
| Medium chain triglyceride | 0.5 |
| Soy lecithin | 5 |
| Sucrose | 10 |
| Benzyl alcohol | 0.9 |
| De-ionized water, qs to | 100 |

\* Phospholipid-to-vitamin K weight ratio = 25:1
\*\* Oil concentration = 1% by weight Procedure 1. Weigh out phytonadione, soybean oil, medium chain triglyceride, Phospholipon 90G and benzyl alcohol in a clean container. Sonicate and gently heat to dissolve all solids to obtain a clear yellow solution.

2. Weigh out sucrose and de-ionized water into another clean container. Mix well to dissolve all solids to obtain a clear colorless solution.

3. Mix the above 2 solutions by agitation to form a crude emulsion and adjust pH to between 6-7 using 1N HCl or NaOH.

4. Homogenize the crude emulsion to a nanoemulsion by using a microfluidizer until the average droplet size, as determined by laser light scattering, is less than 100 nm.

5. Filter the nanoemulsion through a 0.22 μm filter to sterilize the nanoemulsion. Perform this procedure under a nitrogen atmosphere.

6. Aseptically, fill the filtered nanoemulsion into sterile vials.

7. Crimp seal the vials.

The F-1 nanoemulsion thusly prepared is a slightly yellow and transparent/translucent solution.

Example 2

Preparation of F2 Nanoemulsion Containing Vitamin K1

A nanoemulsion containing 0.2% vitamin K1 was prepared using the following composition and the procedure as described in Example 1:

| F-2 composition | |
|---|---|
| Ingredient | % w/w |
| Phytonadione | 0.2 |
| Soybean oil | 0.5 |
| Medium chain triglyceride | 0.5 |
| Soy lecithin | 5 |
| Sucrose | 10 |
| Benzyl alcohol | 0.9 |
| Histidine | 0.31 |
| Water for injection, qs to | 100 |

\* Phospholipid-to-vitamin K weight ratio = 25:1
\*\* Oil concentration = 1% by weight. The F2 nanoemulsion prepared is a slightly yellow and transparent/translucent solution.

Example 3

Preparation of Nanoemulsions Containing 1% Vitamin K1

A nanoemulsion containing 1% vitamin K1 was prepared using the following composition and the procedure as described in Example 1:

| Composition (% w/w) | |
|---|---|
| Ingredient | F2-1a |
| Phytonadione | 1 |
| Soybean oil | 0.5 |
| Medium chain triglyceride | 0.5 |
| Soy lecithin | 15 |
| Sucrose | 10 |
| Benzyl alcohol | 0.9 |
| Histidine | 0.31 |
| Water for injection, qs to | 100 |

\* Phospholipid-to-vitamin K ratio = 15:1
\*\* Oil concentration = 1% by weight
Methionine or ascorbic acid may be optionally added the above compositions.

Example 4

Preparation of a Nanoemulsion Containing Vitamin K2

A nanoemulsion containing vitamin K2 (menaquinone) was prepared using the following composition and the procedure as described in Example 1.

F-3 composition

| Ingredient | % w/w |
|---|---|
| Menaquinone | 1 |
| Soybean oil | 0.5 |
| Medium chain triglyceride | 0.5 |
| Soy lecithin | 15 |
| Sucrose | 10 |
| Benzyl alcohol | 0.9 |
| De-ionized water, qs to | 100 |

\* Phospholipid-to-vitamin K ratio = 15:1
\*\* Oil concentration = 1% by weight

Example 5

Preparation of a Nanoemulsion Containing Vitamin K2

A nanoemulsion containing vitamin K2 (menaquinone) was prepared using the following composition and the procedure as described in Example 1.

| Ingredient | % w/w |
|---|---|
| Menaquinone | 0.2 |
| Soybean oil | 0.5 |
| Medium chain triglyceride | 0.5 |
| Soy lecithin | 5 |
| Sucrose | 10 |
| Benzyl alcohol | 0.9 |
| De-ionized water, qs to | 100 |

\* Phospholipid-to-vitamin K ratio = 25:1
\*\* Oil concentration = 1% by weight

Example 6

Stability of Nanoemulsions Containing Vitamin K1

A lot of F-1 nanoemulsion (lot#111-1-11) was prepared according to Example 1 and tested for long-term stability. The stability tests included (a) appearance, (b) light transmittance@600 nm, pH, vitamin K1 assay and purity by HPLC, and average droplet size as determined by laser light scattering.

| Storage | Initial (Time 0) | 1 month | 2 month | 5 month | 6 month | 12 month | 24 month |
|---|---|---|---|---|---|---|---|
| | | Appearance | | | | | |
| 2-8° C. | Yellow, clear and uniform solution. No visible oil droplets or solid particles | Same as T0 | Same as T0 | Same as T0 | Same as T0 | Same as T0 | Same as T0 |
| 25° C. | | Same as T0 | Same as T0 | Same as T0 | Same as T0 | Same as T0 | Not tested |
| 40° C. | | Same as T0 | Same as T0 | Same as T0 | Same as T0 | Not tested | Not tested |
| Storage | Time 0 | 1 month | 2 month | 5 month | 6 month | 12 month | 24 month |
| | | Light transmittance @ 600 nm | | | | | |
| 2-8° C. | 85.3% | 86.7% | 85.7% | 81.7% | 79.3% | 71.8% | 57.6% |
| 25° C. | | 74.2% | 71.6% | 71.1% | 70.1% | 73.3% | Not tested |
| 40° C. | | 62.4% | 66.8% | 69.6% | 1% | Not tested | Not tested |
| | | pH | | | | | |
| 2-8° C. | 6.34 | 5.64 | 5.63 | 5.76 | 5.95 | 5.43 | 5.13 |
| 25° C. | | 4.71 | 5.01 | 5.16 | 5.09 | 4.67 | Not tested |
| 40° C. | | 4.75 | 4.72 | 4.51 | 3.97 | Not tested | Not tested |
| | | Vitamin K1 assay by HPLC in mg/mL (% of assay over the initial assay value) | | | | | |
| 2-8° C. | 2.14 | 2.10 (98.1) | 2.11 (98.6) | 2.03 (94.9) | 2.07 (96.7) | 1.94 (90.7) | 1.99 (93.0) |
| 25° C. | | 2.10 (98.1) | 2.12 (99.1) | 1.96 (91.6) | 2.01 (94.0) | 1.87 (87.4) | Not tested |
| 40° C. | | 2.06 (96.3) | 2.03 (94.9) | 1.90 (88.8) | 1.87 (87.3) | Not tested | Not tested |
| | | Chromatogram Purity, 330 nm | | | | | |
| 2-8° C. | 92.4 | 97.7 | 98.2 | 87.4 | 96.9 | 92.1 | 94.8 |
| 25° C. | | 97.0 | 97.7 | 87.7 | 97.5 | 92.0 | Not |

-continued

| | | | | | | |
|---|---|---|---|---|---|---|
| 40° C. | | 97.4 | 97.6 | 89.6 | 95.8 | Not tested | Not tested |

Average droplet size (nm in diameter) by laser light scattering

| | | | | | | | |
|---|---|---|---|---|---|---|---|
| 2-8° C. | 86.9 | 86.1 | — | 86.4 | 87.8 | 101 | 104 |
| 25° C. | | 110 | — | 125 | 118 | 128 | Not tested |
| 40° C. | | 155 | — | 174 | 725 | Not tested | Not tested |

Another lot of nanoemulsion (lot#111-1-24) was prepared according to Example 2 and tested for long-term stability. The stability tests include (a) appearance, (b) light transmittance@600 nm, pH, vitamin K1 assay and purity by HPLC, and average droplet size as determined by laser light scattering.

| Appearance: | | | | | | | |
|---|---|---|---|---|---|---|---|
| Storage | Initial (T0) | 1 month | 2 month | 3 month | 9 month | 18 month | 24 month |
| 2-8° C. | Yellow, clear and uniform solution. No visible oil droplets or solid particles | Same as T0 | Same as T0 | Same as T0 | Same as T0 | Same as T0 | Same as T0 |
| 25° C. | | Same as T0 | Same as T0 | Same as T0 | No change | Slightly opaque | Slightly opaque |
| 40° C. | | Same as T0 | Same as T0 | Same as T0 | Not tested | Not tested | Not tested |

| Storage | Time 0 | 1 month | 2 month | 3 month | 9 month | 18 month | 24 month |
|---|---|---|---|---|---|---|---|
| Light transmittance @ 600 nm | | | | | | | |
| 2-8° C. | 81.3% | 79.7% | 80.5% | 72.7% | 71.9% | 62.4% | 61.7% |
| 25° C. | | 66.6% | 64.7% | 66.2% | 70.1% | 73.4% | 74.3% |
| 40° C. | | 59.9% | 61.5% | 63.6% | Not tested | Not tested | Not tested |
| pH | | | | | | | |
| 2-8° C. | 7.09 | 6.97 | 6.64 | 6.51 | 6.45 | 6.41 | 6.38 |
| 25° C. | | 6.87 | 6.65 | 6.58 | 6.31 | 6.38 | 6.45 |
| 40° C. | | 6.70 | 6.69 | 6.61 | Not tested | Not tested | Not tested |
| Vitamin K1 assay by HPLC in mg/mL (% of assay over the initial assay value) | | | | | | | |
| 2-8° C. | 1.94 | 1.96 (101.4) | 1.96 (101.1) | 2.11 (108.8) | 1.91 (98.5) | 1.94 (100) | 1.91 (98.5) |
| 25° C. | | 1.94 (100.1) | 1.89 (97.7) | 1.96 (101.2) | 1.72 (88.7) | 1.63 (84.0) | 1.61 (83.0) |
| 40° C. | | 1.91 (98.9) | 1.73 (89.3) | 1.79 (92.3) | Not tested | Not tested | Not tested |
| Chromatogram Purity, 330 nm | | | | | | | |
| 2-8° C. | 99.9% | 94.5% | 94.7% | 97.3% | 98.6% | 93.5% | 85.9% |
| 25° C. | | 94.6% | 94.3% | 96.4% | 88.6% | 92.7% | 85.2% |
| 40° C. | | 96.0% | 94.5% | 95.1% | Not tested | Not tested | Not tested |
| Average droplet size (nm in diameter) by laser light scattering | | | | | | | |
| 2-8° C. | 83.9 nm | 86.4 | 85.3 | 107 | 98.4 | 105 | 108 |
| 25° C. | | 119 | 112 | 132 | 119 | 120 | 128 |
| 40° C. | | 136 | 136 | 159 | Not tested | Not tested | Not tested |

Conclusion: F-1 and F-2 are physically and chemically stable at 2-8 and 25 deg C.

Example 7

Evaluation of Vein Irritation of F-2 Nanoemulsion Containing Vitamin K1

Methods: Using the standard rabbit marginal ear vein model a lot (lot#111-1-24) of F-2 nanoemulsion containing vitamin K1 prepared according to Example 2 was infused at the maximum clinical concentration (0.6 mg/mL) at a rate of 1.0 mL/min with a dose of 18 mg per rabbit for total eight male New Zealand white rabbits. Injections were given once a day for three consecutive days. The control group was infused with a 5% dextrose solution for injection (D5W).

Figure 3:
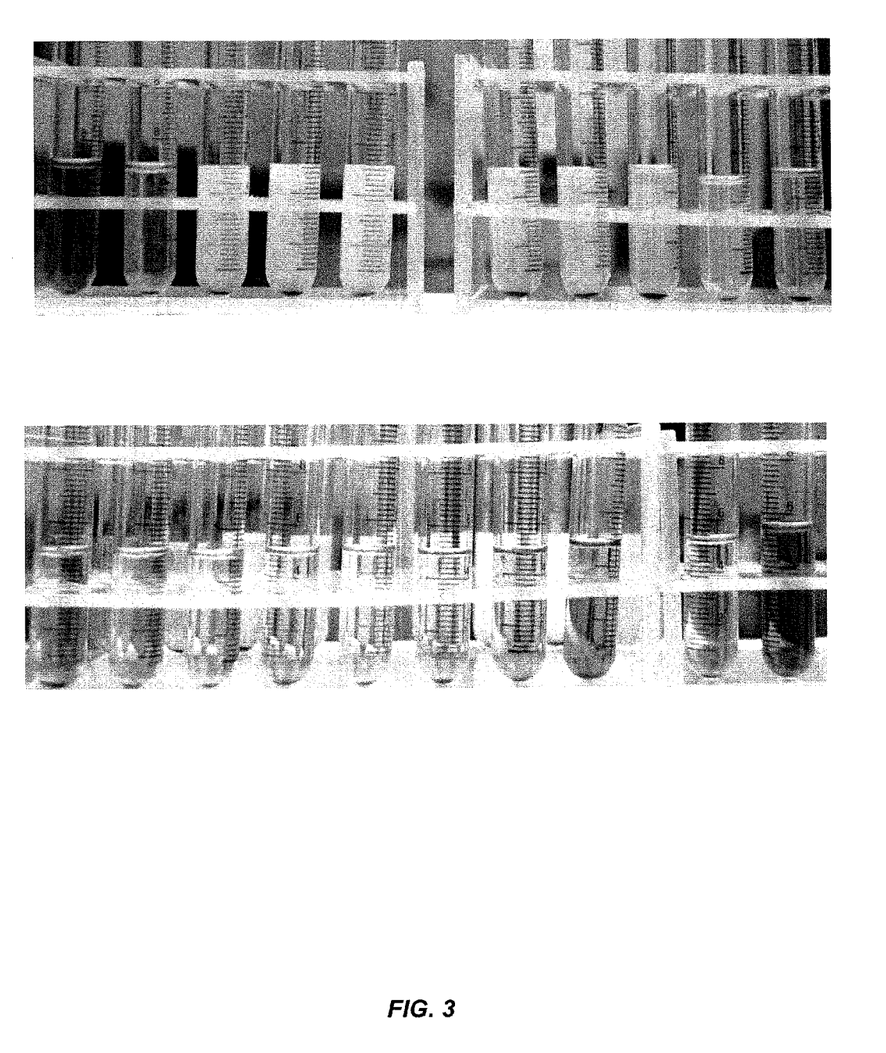
FIG. 3. Hemolysis study. Top panel: From left to right are Tubes #10, 9, 8, 7, 6, 5, 4, 3, 2 and 1. Tubes 1-8 contain F2 nanoemulsion (at 0.04, 0.08, 0.12, 0.16, 0.2, 0.4, 0.6, and 1 mg/mL, respectively), Tube #9 is normal saline (negative control), and Tube #10 is water (positive control). Hemolysis is indicated by red color. None of the F2 nanoemulsion tubes exhibited the red color of the positive control, which indicates hemolysis.

Results: During the infusion, the animals remained quiet and exhibited steady breathing. After each infusion, no edema or redness was observed at the injection site. Forty-eight hours after the last infusion, animals were sacrificed and the marginal ear vein with surrounding tissue from the downstream section of the injection site was removed for histopathologic examination. No tissue inflammation, denaturation, necrosis or other signs of irritation was observed (FIG. 3).

Conclusion: The vitamin K1 nanoemulsion (F-2) does not cause vein irritation and meets the requirement for injection site safety.

Example 8

Evaluation of Hemolytic Potential of F-2 Nanoemulsion Containing Vitamin K1

Method: Visual examination of hemolysis or aggregation, in vitro, in 2% rabbit red blood cells (RBC) suspended in a normal saline solution containing the F-2 vitamin K1 nanoemulsion (lot#111-1-24) prepared according to Example 2. The F-2 nanoemulsion was adjusted to a concentration used clinically and mixed with a 2% rabbit RBC suspension at various ratios (see Table below); the mixtures were then incubated at 37° C. for 3 hours and observed for hemolysis and aggregation. PIE-USP was evaluated in the same way for comparison.

| | Mixing ratios | | | | | | | | | |
|---|---|---|---|---|---|---|---|---|---|---|
| Tube#/mL added | 1 | 2 | 3 | 4 | 5 | 6 | 7 | 8 | 9 | 10 |
| Vit K1 in F-2 nanoemulsion or Phytonadione Injectable Emulsion, USP | 0.1 | 0.2 | 0.3 | 0.4 | 0.5 | 1 | 1.5 | 2.5 | 0 | 0 |
| Normal Saline (negative control) | 2.4 | 2.3 | 2.2 | 2.1 | 2.0 | 1.5 | 1.0 | 0 | 2.5 | 0 |
| Distilled Water (positive control) | 0 | 0 | 0 | 0 | 0 | 0 | 0 | 0 | 0 | 2.5 |
| 2% red blood cells | 2.5 | 2.5 | 2.5 | 2.5 | 2.5 | 2.5 | 2.5 | 2.5 | 2.5 | 2.5 |
| Vit K1 conc (mg/mL) | 0.04 | 0.08 | 0.12 | 0.16 | 0.2 | 0.4 | 0.6 | 1.0 | 0 | 0 |

Results: No hemolysis or aggregation was observed at any mixing ratio or the clinically used concentration for the F-2 nanoemulsion (up to 1 mg/mL vitamin K). In contrast, PIE-USP (a generic formulation of AquaMEPHYTON) was hemolytic at higher concentrations (0.16, 0.2, 0.4, 0.6, and 1 mg/mL, Tubes #4 to #8) (FIG. 4), consistent with its known propensity to be locally irritating following subcutaneous or intramuscular injection.

Conclusion: Vitamin K1 nanoemulsion (F-2) prepared according to this invention is non-hemolytic at up to 1 mg/mL vitamin K and PIE-USP is hemolytic as low as 0.16 mg/mL in the rabbit RBC assay.

Example 9

Hypersensitivity Evaluation for F-2 Nanoemulsion Containing Vitamin K1 Prepared According to Example 2

METHOD: The potential for the F-2 vitamin K nanoemulsion (lot#111-1-24) to induce hypersensitivity was evaluated in guinea pigs following intraperitoneal (IP) sensitization then intravenous challenge with F-2. For a negative control, 0.9% NaCl solution (normal saline) was administered. As a positive control, bovine albumin (BSA) protein (2.5 mg/animal) was injected. Each F-2-treated animal received three IP sensitizing doses prior to being challenged with an intravenous injection of the F-2 vitamin K1 nanoemulsion, normal saline, or BSA then observed for hypersensitivity reactions.

| Model: | Guinea pigs | |
|---|---|---|
| Weight: | 32 (Male), 250-300 g body weight | |
| Group #1: | Negative control (normal saline) | |
| Group #2: | Positive control (bovine serum albumin) | |
| Group #3: | Low dose | |
| | Sensitization: | IP, 4 mg/kg, 3X |
| | Challenge: | IV, 8 mg/kg, 1X |
| Group #4: | High dose | |
| | Sensitization: | IP, 8 mg/kg, 3X |
| | Challenge: | IV, 16 mg/kg, 1X |

RESULTS: None of the animals that were sensitized and challenged with the F-2 nanoemulsion showed any hypersensitivity symptoms or reactions; all animals in this group exhibited normal behavior. The negative control group also showed no hypersensitivity symptoms and exhibited normal behavior. In the positive control group, eight of the 10 animals exhibited behavior and symptoms consistent with allergic reactions: nose scratching, trembling, difficulty in breathing, twitching. Six of the 8 positive control group animals died within one hour of the IV challenge.

CONCLUSION: The F-2 nanoemulsion containing vitamin K1 and prepared according to this invention did not cause any hypersensitivity reactions and was non-allergenic in the test animals.

Example 10

Bioequivalence Demonstration for the F-2 and F-61 Nanoemulsions Containing Vitamin K1

METHOD: A mouse model was employed to compare the vitamin K1 plasma pharmacokinetic profiles of the F-2 nanoemulsion prepared according to Example 2 (lot#111-1-24) and PIE-USP (a generic version of AquaMEPHYTON). Each animal received a 0.1 mL tail vein injection of F-2 nanoemulsion or PIE-USP. Blood samples were taken at 0.25, 0.5, 1, 2, 3, 6, 12 and 24 hours. For each time-point, blood samples from four mice were collected and analyzed for vitamin K1 concentration by an LC-MS/MS method.

Another two nanoemulsion compositions were prepared (F-61) to have the following compositions using the same method as described in Example 1. Although they differed in vitamin K1 strength, the two F-61 nanoemulsions had the same phospholipid-to-vitamin K weight ratio of 13:1 and oil concentration of 0.1% by weight and possessed the same very high transparency (T750>90%) and small droplets (<80 nm).

| F-61 composition | | |
|---|---|---|
| Component | 10 mg/mL strength Lot# 144-1-1 | 2 mg/mL strength Lot# 144-1-17 |
| Phytonadione (Purity = 98.0%) | 1.02 | 0.204 |
| Soybean oil (Super-refined) | 0.05 | 0.05 |
| Medium chain triglyceride | 0.05 | 0.05 |
| Soy lecithin | 13.00 | 13.00 |
| L-histidine | 0.11 | 0.11 |
| Sucrose | 10.00 | 10.00 |
| Water for Injection (WFI), to qs | 100 | 100 |
| pH (adjusted with a 1N HCl/NaOH) | 6.5 +/− 0.2 | 6.5 +/− 0.2 |
| T750 | 92.0 | 94.8 |
| Average droplet size (nm in dia) | 79.4 | 72.4 |

Figure 5:
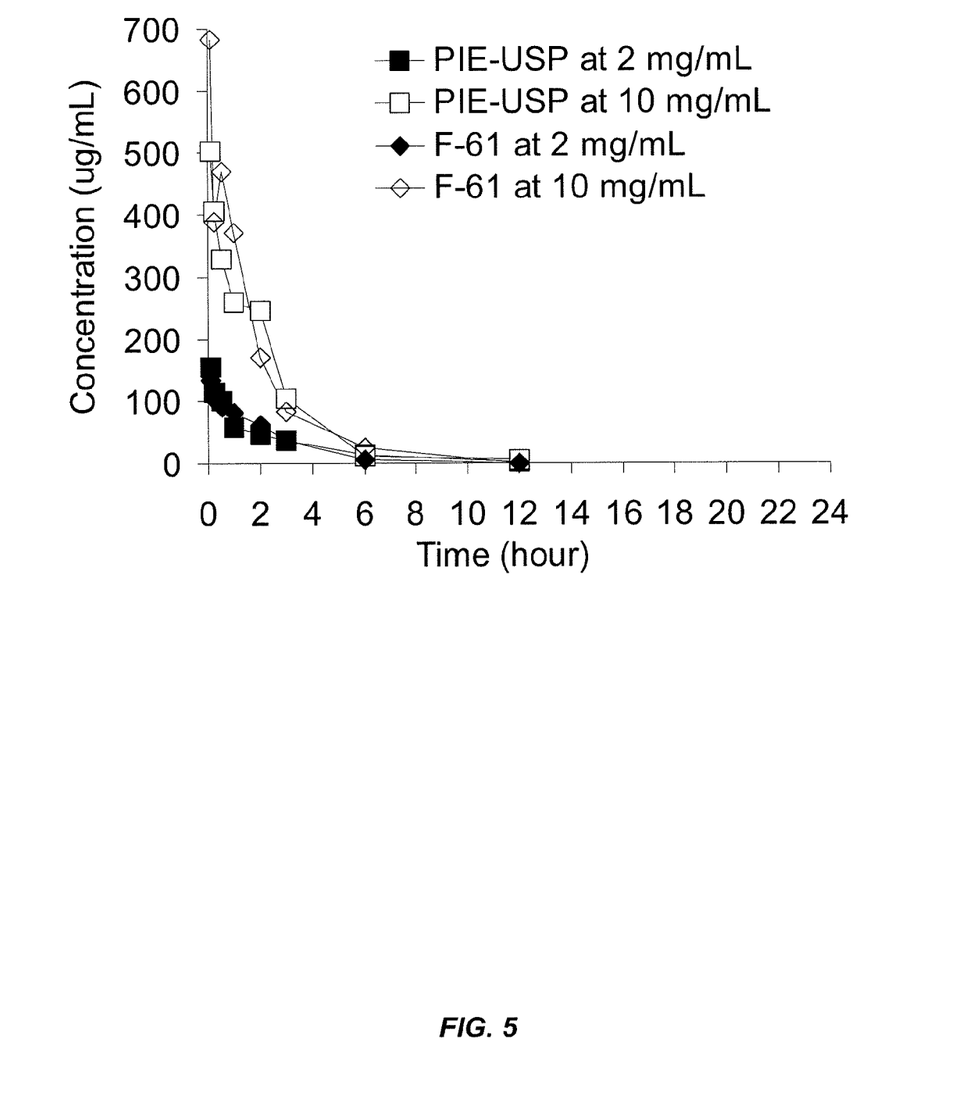
FIG. 5. Mouse plasma pharmaocokinetic profiles of F-61 nanoemulsions at 2 mg/mL and 10 mg/mL as compared to PIE-USP formulations at the same strengths. The diamonds denote the F-61 nanoemulsion and squares the PIE-USP profiles.

The two F-61 nanoemulsions were also tested for their pharmacokinetic profiles in mice using the similar conditions as for F-1 and were compared with PIE-USP at the same vitamin K1 strengths (2 mg/mL, lot#88-127-EV and 10 mg/mL. lot#88-130-EV, both by Hospira) to determine bioequivalence (FIG. 5).

Figure 4:
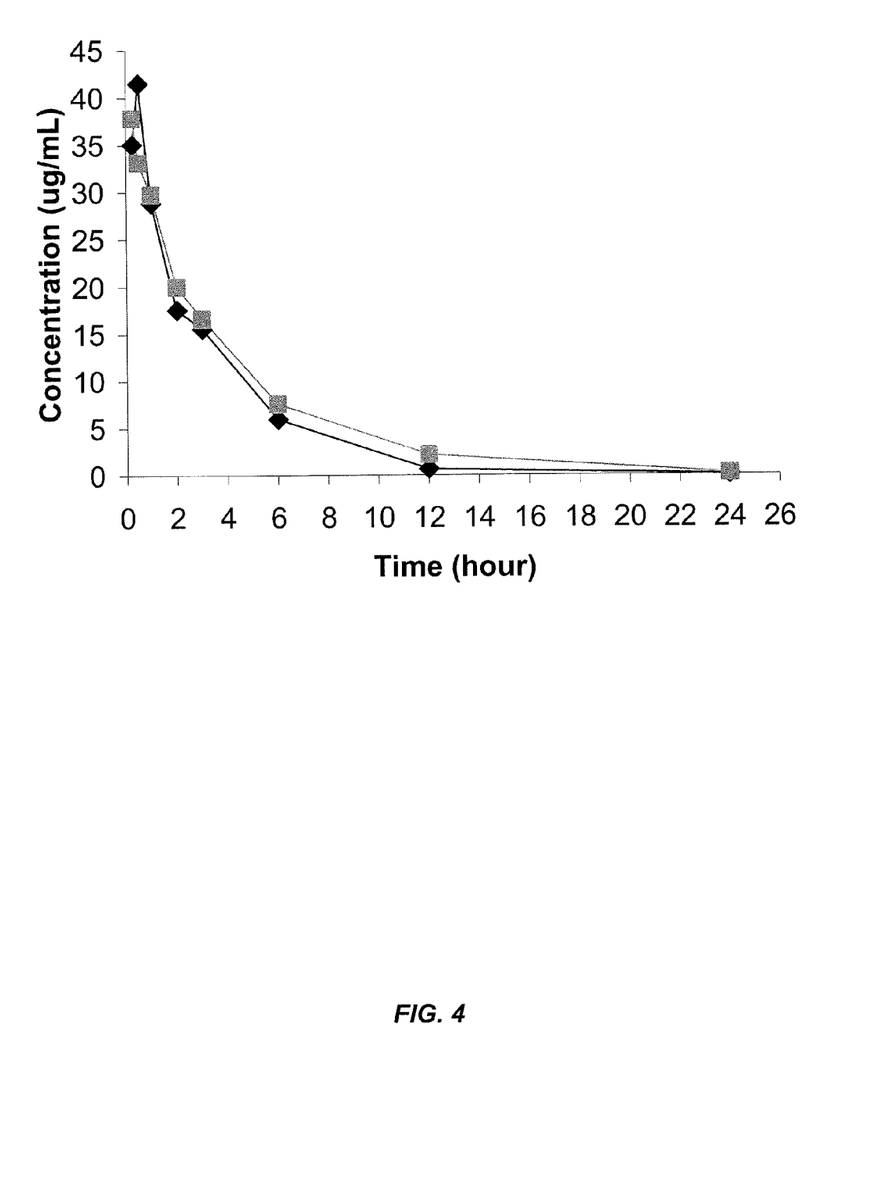
FIG. 4. Mouse pharmacokinetic profile of F-2 nanoemulsion (prepared according to Example 10) compared to pharmacokinetic profile of PIE-USP at the same strength. The diamonds denote plasma vitamin K levels in the F-1 nanoemulsion-treated mice and squares from the PIE-USP-treated mice.

RESULTS: FIG. 4 shows the plasma pharmacokinetic profiles of F-2 and FIG. 5 the F-61 nanoemulsions in comparison with their respective PIE-USP reference drugs.

CONCLUSION: The overlapping plasma pharmacokinetic profiles for F-2 and PIE-USP at 2 mg/mL, F-61 at 2 mg/mL and PIE-USP at 2 mg/mL and F-61 at 10 mg/mL and PIE-USP at 10 mg/mL demonstrate that the nanoemulsions prepared according to this invention are bioequivalent to the Phytonadione Injectable Emulsion, USP formulations of the same strength.

Example 11

Physical Stability of the F-1 Nanoemulsion Prepared According to Example 1 (Lot#111-1-11) Compared with the Vitamin K1 Composition Disclosed in U.S. Pat. No. 5,021,570 (lot#111-1-53) After Freeze-Thaw Treatment A vitamin K emulsion was prepared according to U.S. Pat. No. 5,021,570 having the following composition:

| Ingredient | % (w/w) | mg/g | mg per batch |
|---|---|---|---|
| Phytonadione | 0.5 | 5 | 5 |
| Hydrogenated lecithin | 0.8 | 8 | 8 |
| Sesame Oil | 0.2 | 2 | 2 |
| Glycerol | 5 | 50 | 50 |
| Sorbitol | 5 | 50 | 50 |

-continued

| Ingredient | % (w/w) | mg/g | mg per batch |
|---|---|---|---|
| Taurine | 0.3 | 3 | 3 |
| DI-water | 88.2 | 882 | 882 |
| Total | 100 | 1000 | 1000 | pH 7.2 +/− 0.1

The physical stability of these emulsions were tested and compared as follow:
1. Transfer 1 mL of an emulsion into a 2 mL glass vial.
2. Take photographs.
3. Observe the emulsions under a microscope and take photographs.
4. Measure light transmittance of at 600 nm using a UV-visible spectrophotometer.
5. Freeze the emulsions at −20° C. overnight.
6. Thaw the emulsions and allow them to come to room temperature.
7. Repeat steps 2 to 4.

The freeze-thaw stability results are shown in the following tables:

| | Light transmittance (%) | |
|---|---|---|
| Sample ID | Before freeze-thaw 600 nm | After freeze-thaw 600 nm |
| DI-water | 100.2 | 100.0 |
| F-1 | 80.2 | 75.5 |
| U.S. Pat. No. 5,021,570 | 16 | 2.0 |

| | Appearance | | | |
|---|---|---|---|---|
| | Visual | | Microscope | |
| Sample ID | Time 0 | Freeze-thaw | Time 0 | Freeze-thaw |
| F-1 | Yellow, translucent | Yellow, translucent | Clear | Clear |
| U.S. Pat. No. 5,021,570 | Yellow, opaque | Yellow, opaque | Opaque | Opaque |

Conclusion: F-1 nanoemulsion remained translucent, demonstrating that it retained its stability following a freeze-thaw cycle. In contrast, the prior art vitamin K1 emulsion produced according to U.S. Pat. No. 5,021,570 was opaque, did not transmit light and was not stable after a freeze-thaw treatment.

Example 12

Stability of Vitamin K1 Nanoemulsion Compared with PIE-USP Under Heat Stress Conditions Two nanoemulsion compositions (F-10A and F-10B) were prepared with the following compositions according to the method described in Example 1.

| | Composition, % w/w | |
|---|---|---|
| Ingredient | F-10A | F-10B |
| Phytonadione | 0.20 | 0.20 |
| Soybean oil | 0.50 | 0.50 |
| Medium chain triglyceride | 0.50 | 0.50 |
| Soy lecithin | 5.0 | 5.0 |

-continued

| Composition, % w/w | | |
|---|---|---|
| Ingredient | F-10A | F-10B |
| Vitamin E | 0.07 | 0.07 |
| Sucrose | 10.0 | 10.0 |
| Benzyl Alcohol | 0.90 | 0.90 |
| Histidine | 0.31 | 0.31 |
| Methionine | 0.30 | |
| Ascorbic acid | | 0.20 |
| Water for Injection | 82.22 | 82.32 |

The F-10A and F-10B vitamin K1 nanoemulsions and the commercial drug product PIE-USP (Hospira lot 81-345-EV) were autoclaved then placed into stability chambers at 40° C. and 60° C. After 1 and 2-weeks in storage, each formulation was tested for phytonadione concentration and appearance. The results are shown in the tables below:

| Phytonadione concentration (mg/g) by HPLC | | | | | | |
|---|---|---|---|---|---|---|
| | | After Auto- | 1 Week | | 2 Weeks | |
| ID | $T_0$ | claving | 40° C. | 60° C. | 40° C. | 60° C. |
| F-10A | 2.05 | 1.98 | 1.97 | 1.86 | 1.79 | 1.00 |
| F-10B | 2.04 | 1.93 | 1.99 | 1.97 | 1.85 | 1.91 |
| PIE-USP | 2.02 | 1.91 | 2.03 | 2.00 | 1.79 | 1.84 |

| | | After Auto- | 1 Week | | 2 Weeks | |
|---|---|---|---|---|---|---|
| ID | $T_0$ | claving | 40° C. | 60° C. | 40° C. | 60° C. |
| Phytonadione concentration recovery (% over $T_0$) | | | | | | |
| F10A | 100 | 96.6 | 96.2 | 91.0 | 87.3 | 49.0 |
| F10B | 100 | 94.6 | 97.5 | 96.2 | 90.6 | 93.6 |
| PIE-USP | 100 | 94.6 | 100.4 | 99.3 | 88.8 | 91.2 |
| Appearance | | | | | | |
| F-10A | Light yellow, translucent | No change | No change | Slightly darker | No change | Slightly darker |
| F-10B | Light yellow, translucent | Slightly darker | Slightly darker | Darker | Slightly darker | Darker |
| PIE-USP | Light yellow, transparent | No change | No change | No change | No change | No change |

Conclusion: F-10B exhibited a slightly greater recovery of phytonadione concentration than the PIE-USP after 2 weeks at 60° C. The change in appearance in F-10B was most likely due to oxidation of ascorbic acid under the extensive heat stress.

Example 13

Preparation of Nanoemulsions Containing Vitamin K Having Exceptionally High Transparency and Stability The following studies were conducted in a continuing effort to define the acceptable ranges for the phospholipid-to-vitamin K weight ratio and oil concentration for compositions having the desired droplet size (<150 nm), transparency (T600 or T750>20%) and stability (comparable to or better than PIE-USP)

Study #1

Objective: To investigate transparency, droplet size and viscosity in an emulsion with the phospholipid-to-vitamin K weight ratio less than 13:1 and/or oil concentration greater than 1% by weight.

The following compositions were prepared using a procedure similar to Example 1 and tested for appearance, transparency and viscosity.

| Compositions | | | | |
|---|---|---|---|---|
| % w/w | F-11 | F-12 | F-13B | F-14 |
| Phytonadione | 1 | 1 | 1 | 1 |
| Soybean oil | 0.5 | 0.75 | 1 | 1.25 |
| Medium chain triglyceride | 0.5 | 0.75 | 1 | 1.25 |
| Soy lecithin | 5 | 7.5 | 10 | 12.5 |
| Vitamin E | 0.07 | 0.07 | 0.07 | 0.07 |
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Ascorbic acid | 0.2 | 0.2 | 0.2 | 0.2 |
| Water for injection, qs to | 100 | 100 | 100 | 100 |
| Phospholipid-to-vitamin K weight ratio | 5:1 | 7.5:1 | 10:1 | 12.5:1 |
| Oil concentration (% wt) | 1 | 1.5 | 2 | 2.5 |

| Results | | | | |
|---|---|---|---|---|
| Appearance | Yellow, opaque liquid | Yellow, opaque liquid | Yellow, opaque, liquid | Yellow, opaque, liquid |
| Droplet Size (nm, diameter) | 214 | 286 | 319 | 288 |
| T600 (%) | 17.4 | 19.1 | 1.0 | 18.8 |
| Other observation | Viscous | Viscous | Viscous | Viscous |

Conclusion: Compositions with phospholipid-to-vitamin K weight ratio less than 13:1 and/or oil concentration greater than 1% by weight are visually opaque, of high droplet size (>150 nm), low transparency and viscous (the latter being unsuitable for injection).

Study #2

Objectives: To determine the acceptable ranges for phospholipid-to-vitamin K weight ratio and oil concentration used to achieve high transparency.

The following compositions were prepared using a procedure similar to Example 1 and tested for appearance, transparency and viscosity.

| Composition | | | | |
|---|---|---|---|---|
| % w/w | F-22 | F-23 | F-24 | F-25 |
| Phytonadione | 1 | 1 | 1 | 1 |
| Soybean oil | 0 | 0 | 0 | 0 |
| Medium chain triglyceride | 0 | 0 | 0 | 0 |
| Soy lecithin | 15 | 16 | 17 | 18 |
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Water for injection, to qs | 100 | 100 | 100 | 100 |

| % w/w | F-29 | F-30 | F-31 | F-32 |
|---|---|---|---|---|
| Phytonadione | 1 | 1 | 1 | 1 |
| Soybean oil | 0.05 | 0.05 | 0.05 | 0.05 |
| Medium chain triglyceride | 0.05 | 0.05 | 0.05 | 0.05 |
| Soy lecithin | 15 | 16 | 17 | 18 |
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Water for injection, to qs | 100 | 100 | 100 | 100 |

| % w/w | F-36 | F-37 | F-38 | F-39 |
|---|---|---|---|---|
| Phytonadione | 1 | 1 | 1 | 1 |
| Soybean oil | 0.1 | 0.1 | 0.1 | 0.1 |
| Medium chain triglyceride | 0.1 | 0.1 | 0.1 | 0.1 |
| Soy lecithin | 15 | 16 | 17 | 18 |

-continued

|  | | | | |
|---|---|---|---|---|
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Water for injection, to qs | 100 | 100 | 100 | 100 |

| % w/w | F-43 | F-44 | F-45 | F-46 |
|---|---|---|---|---|
| Phytonadione | 1 | 1 | 1 | 1 |
| Soybean oil | 0.25 | 0.25 | 0.25 | 0.25 |
| Medium chain triglyceride | 0.25 | 0.25 | 0.25 | 0.25 |
| Soy lecithin | 15 | 16 | 17 | 18 |
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Water for injection, to qs | 100 | 100 | 100 | 100 |

| % w/w | F-50 | F-51 | F-52 | F-53 |
|---|---|---|---|---|
| Phytonadione | 1 | 1 | 1 | 1 |
| Soybean oil | 1 | 1 | 1 | 1 |
| Medium chain triglyceride | 1 | 1 | 1 | 1 |
| Soy lecithin | 15 | 16 | 17 | 18 |
| Benzyl Alcohol | 0.9 | 0.9 | 0.9 | 0.9 |
| Sucrose | 10 | 10 | 10 | 10 |
| Histidine | 0.31 | 0.31 | 0.31 | 0.31 |
| Water for injection (WFI), to qs | 100 | 100 | 100 | 100 |

Results

| ID | Phospholipid-to-vitamin K wt ratio | Visual transparency ranking* | T600 (%) | T750 (%) |
|---|---|---|---|---|
| At 0% Oil (soybean oil + medium chain triglyceride) | | | | |
| F-20 | 13:1 | 1 | 88.5 | 95.0 |
| F-21 | 14:1 | 1 | 86.9 | 93.9 |
| F-22 | 15:1 | 1 | 88.5 | 95.1 |
| F-23 | 16:1 | 1 | 86.2 | 93.5 |
| F-24 | 17:1 | 2 | 81.3 | 90.2 |
| F-25 | 18:1 | 1 | 87.1 | 94.0 |
| 0.1% Oil (soybean oil + medium chain triglyceride) | | | | |
| F-27 | 13:1 | 3 | 78.0 | 88.4 |
| F-28 | 14:1 | 3 | 76.5 | 87.3 |
| F-29 | 15:1 | 4 | 72.9 | 84.6 |
| F-30 | 16:1 | 3 | 74.2 | 85.6 |
| F-31 | 17:1 | 2 | 80.6 | 89.9 |
| F-32 | 18:1 | 2 | 82.2 | 90.7 |
| 0.2% Oil (soybean oil + medium chain triglyceride) | | | | |
| F-34 | 13:1 | 2 | 87.5 | 94.5 |
| F-35 | 14:1 | 2 | 86.0 | 93.5 |
| F-36 | 15:1 | 2 | 86.5 | 93.6 |
| F-37 | 16:1 | 2 | 86.2 | 93.5 |
| F-38 | 17:1 | 3 | 84.6 | 92.5 |
| F-39 | 18:1 | 4 | 80.2 | 89.5 |
| 0.5% Oil (soybean oil + medium chain triglyceride) | | | | |
| F-41 | 13:1 | 4 | 27.5 | 40.3 |
| F-42 | 14:1 | 2 | 89.7 | 95.5 |
| F-43 | 15:1 | 2 | 81.9 | 90.6 |
| F-44 | 16:1 | 2 | 86.5 | 93.8 |
| F-45 | 17:1 | 2 | 85.9 | 93.4 |
| F-46 | 18:1 | 2 | 85.7 | 93.3 |
| 2% Oil (soybean oil + medium chain triglyceride) | | | | |
| F-48 | 13:1 | 5 | 1.8 | 2.3 |
| F-49 | 14:1 | 5 | 2.0 | 2.8 |
| F-50 | 15:1 | 5 | 2.2 | 2.8 |
| F-51 | 16:1 | 5 | <2 | <2 |
| F-52 | 17:1 | 5 | <2 | <2 |
| F-53 | 18:1 | 5 | <2 | <2 |

*Visual transparency ranking: 1-5, 1 being the best (clear) and 5 being the worst (opaque).
Note:
F-51, F-52 and F-53 were very viscous Conclusion: Compositions with phospholipid-to-vitamin K weight ratio at 13:1, 14:1, 15:1, 16:1, 17:1 and 18:1 AND oil concentration of no more than 1% achieved high transparency with T600/750>20% for all or >70% for most of the samples. Once the oil concentration reached 2%, the compositions became opaque with T600/750 being <20% (F48, F-49, F-50, F-51, F-52 to F-53) and too viscous for injection (F-51 to F-53).

Study #3

Objectives: To determine and compare physical stability of F-20, F-21, F-22 and F-34, F-35, F-36 under freeze-thaw stress or after storage at 40° C.

Procedure: Use the F-20, F-21, F-22 and F-34, F-35, F-36 prepared in Study #2. Apply freeze-thaw stress as follows:
1. Transfer 100 µL it of each formulation into an Eppendorf vial.
2. Freeze at −30° C. and thaw to room temperature. Repeat for a total of three freeze-thaw cycles.

Results

Droplet size by Laser Light Scattering (LLS)

| ID | Phospholipid-to-vitamin K wt ratio/Oil conc (% wt) | Treatment | Droplet size (Average dia in nm) |
|---|---|---|---|
| F-20 | 13:1/0% | Before freeze-thaw | 125 |
| | | After 3 freeze-thaws | 122 |
| F-21 | 14:1/0% | Before freeze-thaw | 126 |
| | | After 3 freeze-thaws | 127 |
| F-22 | 15:1/0% | Before freeze-thaw | 125 |
| | | After 3 freeze-thaws | 124 |
| F-34 | 13:1/0.2% | Before freeze-thaw | 158 |
| | | After freeze-thaw | 146 |
| F-35 | 14:1/0.2% | Before freeze-thaw | 140 |
| | | After 3 freeze-thaws | 132 |
| F-36 | 15:1/0.2% | Before freeze-thaw | 136 |
| | | After 3 freeze-thaws | 136 |

Transmittance for F-22 and F-36 after storage at 40° C. for 5 days

| ID | Phospholipid-to-vitamin K wt ratio/Oil conc (% wt) | Appearance | T600 (%) | T750 (%) |
|---|---|---|---|---|
| F-20 | 13:1/0% | No Change | 89.3 | 95.4 |
| F-21 | 14:1/0% | No Change | 87.0 | 93.7 |
| F-22 | 15:1/0% | No Change | 89.6 | 95.4 |
| F-34 | 13:1/0.2% | No Change | 88.2 | 95.2 |
| F-35 | 14:1/0.2% | No Change | 86.3 | 94.1 |
| F-36 | 15:1/0.2% | No Change | 86.8 | 94.2 |

Conclusion: Nanoemulsion compositions comprising phospholipid-to-vitamin K weight ratios of 13:1, 14:1 and 15:1 and oil concentrations of no more than 1% by weight are surprisingly transparent and physically stable against freeze-thaw and high temperature stress.

Study #4

Objectives: To determine effects of soy lecithin type, benzyl alcohol, histidine, vitamin E, and nitrogen gas on stability of phytonadione in nanoemulsions comprising phospholipid-to-vitamin K weight ratio of 13:1 and oil concentration of 0.1% by weight.

The following compositions were prepared using a procedure similar to Example 1 and tested for chemical stability of phytonadione in the nanoemulsion by measuring the recovered phytonadione by HPLC analysis after the nanoemulsions were stored under heated conditions.

| Composition | | | | | | | |
|---|---|---|---|---|---|---|---|
| % w/w | F-54 | F-55 | F-56 | F-57 | F-58 | F-59 | F-60 |
| Phytonadione | 1 | 1 | 1 | 1 | 1 | 1 | 0.2 |
| Soybean Oil | 0.05 | 0.05 | 0.05 | 0.05 | 0.05 | 0.05 | 0.05 |
| Medium chain triglyceride | 0.05 | 0.05 | 0.05 | 0.05 | 0.05 | 0.05 | 0.05 |
| Soy lecithin (Phospholipon 90G) | 13 | 0 | 13 | 13 | 13 | 13 | 13 |
| Soy lecithin (Lipoid S100) | 0 | 13 | 0 | 0 | 0 | 0 | 0 |
| Benzyl Alcohol | 0 | 0 | 0.9 | 0 | 0 | 0 | 0 |
| Histidine | 0 | 0 | 0 | 0.11 | 0 | 0 | 0 |
| Vitamin E | 0 | 0 | 0 | 0 | 0.07 | 0 | 0 |
| Sucrose | 10 | 10 | 10 | 10 | 10 | 10 | 10 |
| WFI | 75.9 | 75.9 | 75 | 75.79 | 75.83 | 75.9 | 76.7 |
| $N_2$ gas in head space | No | No | No | No | No | Yes | No |

Results
Phytonadione Concentration by HPLC analysis (mg/g)

| ID | | Initial (T0) | Auto-claved | 1 Week @ 60° C. | 2 Weeks @ 60° C. | 2 Weeks @ 40° C. |
|---|---|---|---|---|---|---|
| F-54 | Phospholipon 90G | 9.96 | 9.77 | 9.83 | 9.36 | 9.82 |
| F-55 | Lipoid S100 | 9.89 | 9.81 | 9.63 | 8.78 | 9.82 |
| F-56 | Benzyl Alcohol | 10.04 | 9.87 | 9.93 | 9.71 | 9.88 |
| F-57 | Histidine | 10.04 | 9.94 | 10.08 | 9.88 | 10.03 |
| F-58 | Vitamin E | 9.92 | 9.70 | 9.64 | 9.43 | 9.78 |
| F-59 | N2 | 10.18 | 9.85 | 9.88 | 9.67 | 10.36 |
| F-60 | 2 mg/g | 2.07 | 1.99 | 1.95 | 1.71 | 2.01 |
| F-1 * | 2 mg/g | 1.93 | 1.86 | 1.64 | 1.24 | 1.88 |
| PIE-USP** | 2 mg/mL | 2.02 | 2.04 | 2.07 | 2.02 | NA |

Phytonadione Recovery (% over T0)

| ID | | T0 | Auto-claved | 1 Week 60° C. | 2 Weeks 60° C. | 2 Weeks 40° C. |
|---|---|---|---|---|---|---|
| F-54 | Phospholipon 90G | 100 | 98.1 | 98.7 | 94.0 | 98.6 |
| F-55 | Lipoid S100 | 100 | 99.2 | 97.4 | 88.8 | 99.3 |
| F-56 | Benzyl Alcohol | 100 | 98.3 | 98.9 | 96.7 | 98.4 |
| F-57 | Histidine | 100 | 99.0 | 100.3 | 98.3 | 99.9 |
| F-58 | Vitamin E | 100 | 97.7 | 97.2 | 95.1 | 98.6 |
| F-59 | N2 | 100 | 96.8 | 97.1 | 95.1 | 101.8 |
| F-60 | 2 mg/g | 100 | 96.2 | 94.3 | 82.4 | 97.1 |
| F-1 | 2 mg/g | 100 | 96.4 | 85.1 | 63.9 | 97.5 |
| PIE-USP | 2 mg/mL | 100 | 100.9 | 102.5 | 100.3 | NA |

\* As in Example 1.
\*\*2 mg/mL Phytonadione Injectable Emulsion, USP, from Hospira lot 81-345-EV Conclusion
1. Histidine is beneficial for phytonadione stability.
2. F-57 (with histidine) has stability that is comparable to PIE-USP.
3. Different types of soy lecithin (from different sources) can be used to prepare the nanoemulsions with comparable properties.

Example 14

Preparation of Nanoemulsions Comprising a Phospholipid-to-Vitamin K Weight Ratio of 13:1, an Oil Concentration of 0.1% and Other Phospholipids, Oil, Cryoprotectant and Stabilizers

| Ingredient (%) | F-101 | F-102 | F-103 | F-104 | F-105 | F-106 | F-107 | F-108 | F-107 | F-108 |
|---|---|---|---|---|---|---|---|---|---|---|
| Phytonadione | 0.2 | 0.2 | 0.2 | 0.2 | 0.2 | 0.2 | 0.2 | 0.2 | 0.2 | 0.2 |
| Soybean oil | 0.1 | | | | 0.1 | 0.1 | 0.1 | 0.05 | 0.05 | |
| Sesame oil | | 0.1 | | | | | | | | |
| Tricaprylin | | | 0.1 | | | | | | | |
| Medium chain triglyceride | | | | 0.1 | | | | 0.05 | 0.05 | 0.1 |
| Soy lecithin | | 6.5 | 13 | 13 | | | | | | |
| Egg lecithin | 13 | 6.5 | | | | | | 13 | | |
| 1,2-dimyristoyl-sn-glycero-3-phsophocholine (DMPC) | | | | | 13 | | | | 13 | 13 |
| 1,2-distearoyl-sn-glycero-3-phosphoglycerol (DSPG) | | | | | | 13 | | | | |

-continued

| Ingredient (%) | F-101 | F-102 | F-103 | F-104 | F-105 | F-106 | F-107 | F-108 | F-107 | F-108 |
|---|---|---|---|---|---|---|---|---|---|---|
| 1-palmitoyl-2-oleoyl-sn-glycero-3-phosphocholine (POPC) | | | | | | | 13 | | | |
| Glycerin | 2.25 | 2.25 | 2.25 | 2.25 | 2.25 | 2.25 | 2.25 | 2.25 | 2.25 | 2.25 |
| Sodium edetate | 0.005 | | | | | | | | | |
| Methyl paraben | | 0.1 | | | | | | | | |
| Water, to qs | 100 | 100 | 100 | 100 | 100 | 100 | 100 | 100 | 100 | 100 |

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A transparent or translucent nanoemulsion composition, the composition comprising:
   i) vitamin K at about 0.1% to 2% by weight of the nanoemulsion;
   ii) a phospholipid, wherein the phospholipid is about 4% to about 16% by weight of the nanoemulsion, wherein the phospholipid is a member selected from the group consisting of soy lecithin, egg lecithin and a combination thereof;
   iii) a triglyceride oil, wherein, the oil concentration is no more than 1% by weight of the nanoemulsion, wherein the oil droplets of said composition have an average diameter of less than 200 nanometers; wherein said transparent or translucent composition exhibits a light transmittance value at 600 nm of no less than 20%, and wherein the composition is free of surfactants of high hydrophobic lipophilic balance value (HLB value >7).

2. The composition according to claim 1, wherein said composition is bioequivalent to the Phytonadione Injectable Emulsion, USP.

3. The composition according to claim 1, wherein after said composition is stored at 25° C. for 3 months or undergoes a freeze-thaw treatment, the oil droplets of said composition have an average diameter of less than 200 nanometers and said composition exhibits a light transmittance value at 600 nm or 750 nm of no less than 20%.

4. The composition according to claim 1, wherein the vitamin K is selected from the group consisting of vitamin $K_1$, vitamin $K_2$, vitamin $K_3$, vitamin $K_4$, vitamin $K_5$, vitamin $K_6$, vitamin $K_7$, and a combination thereof.

5. The composition according to claim 1, wherein the triglyceride oil is selected from the group consisting of soybean oil, sesame oil, a medium-chain triglyceride, tricaprylin, or a combination thereof.

6. The composition according to claim 1 that additionally comprises a pharmaceutically acceptable cryoprotectant, a preservative, or a stabilizer.

7. The composition according to claim 6, wherein the cryoprotectant is sucrose or glycerin; wherein the preservative is benzyl alcohol, an edetate or paraben; and wherein the stabilizer is histidine, methionine or vitamin E.

8. The composition according to claim 1, wherein the said composition is not vein irritating, non-hemolytic and non-allergenic.

9. A method for treating haemorrhagic disease of a newborn comprising: administering an effective amount of the nanoemulsion composition of claim 1 to the newborn in need thereof.

10. A method for treating blood coagulation disorder in adults, comprising: administering an effective amount of the nanoemulsion composition of claim 1 to the adults in need thereof; wherein the blood coagulation disorder is a member selected from the group consisting of (i) anticoagulant-induced prothrombin deficiency caused by coumarin or indanedione derivatives; (ii) hypoprothrombinemia due to antibacterial therapy; and (iii) hypothrombinemia secondary to factors limiting absorption or synthesis of vitamin K.

11. A kit comprising a composition of claim 1.

12. The composition of claim 1, wherein the phospholipid-to-vitamin K weight ratio is between 13:1 and 25:1.

* * * * *